(12) United States Patent
Buerger et al.

(10) Patent No.: US 8,252,348 B2
(45) Date of Patent: Aug. 28, 2012

(54) COSMETIC PREPARATION COMPRISING HYALURONIC ACID

(75) Inventors: Anette Buerger, Hamburg (DE); Stefan Gallinat, Wedel (DE); Sabine Faenger, Hamburg (DE); Alexander Filbry, Hamburg (DE); Christopher Mummert, Bienbuettel (DE)

(73) Assignee: Beiersdorf AG, Hamburg (DE)

( * ) Notice: Subject to any disclaimer, the term of this patent is extended or adjusted under 35 U.S.C. 154(b) by 929 days.

(21) Appl. No.: 11/908,335

(22) PCT Filed: Nov. 1, 2005

(86) PCT No.: PCT/EP2005/055677
§ 371 (c)(1),
(2), (4) Date: Jan. 10, 2008

(87) PCT Pub. No.: WO2006/018454
PCT Pub. Date: Feb. 23, 2006

(65) Prior Publication Data
US 2008/0306021 A1 Dec. 11, 2008

(30) Foreign Application Priority Data
Mar. 16, 2005 (DE) .......................... 10 2005 012 554

(51) Int. Cl.
*A61K 36/889* (2006.01)
(52) U.S. Cl. ...................................... 424/727
(58) Field of Classification Search .................. None
See application file for complete search history.

(56) References Cited

U.S. PATENT DOCUMENTS

| 5,663,160 A | 9/1997 | Meybeck et al. |
| 6,147,054 A | 11/2000 | De Paoli |
| 2002/0015743 A1 | 2/2002 | Meybeck et al. |
| 2003/0165456 A1 | 9/2003 | Duffy et al. |
| 2006/0018869 A1 | 1/2006 | Stab et al. |

FOREIGN PATENT DOCUMENTS

| CA | 2 322 587 | | 9/1999 |
| DE | 44 10 778 | | 10/1995 |
| DE | 697 20 978 | | 9/1997 |
| DE | 698 19 006 | | 2/1999 |
| DE | 10301632 A1 | * | 7/2004 |
| EP | 0 852 946 | | 7/1998 |
| FR | 2 746 316 | | 9/1997 |
| FR | 2 767 059 | | 2/1999 |
| FR | 2 791 260 | | 9/2000 |
| FR | 2 848 116 | | 6/2004 |
| JP | 8-217660 | | 8/1996 |
| JP | 11-35445 | | 2/1999 |
| JP | 11035445 A | * | 2/1999 |

OTHER PUBLICATIONS

English language abstract of FR 2 848 116.
English language abstract of FR 2 791 260.
English language abstract of FR 2 746 316.
English language abstract of FR 2 767 059.
English language abstract of JP 11-35445.
English language abstract of JP 8-217660.
English language abstract of DE 44 10 778.
English language abstract of the Canadian family member of DE 697 20 978.

* cited by examiner

*Primary Examiner* — Amy L Clark
(74) *Attorney, Agent, or Firm* — Abel Law Group, LLP

(57) ABSTRACT

The present invention relates to cosmetic preparations with an active substance combination of hyaluronic acid and saponins.

20 Claims, No Drawings

COSMETIC PREPARATION COMPRISING HYALURONIC ACID

CROSS-REFERENCE TO RELATED APPLICATIONS

The present application is a U.S. National Stage of International Application No. PCT/EP2005/055677, filed Nov. 1, 2005, which claims priority of German Patent Application No. 10 2005 012 554.9, filed Mar. 16, 2005.

BACKGROUND OF THE INVENTION

1. Field of the Invention

The present invention relates to cosmetic preparations with an active substance combination of hyaluronic acid and saponins.

2. Discussion of Background Information

The desire to appear beautiful and attractive is naturally rooted in man. Even if the beauty ideal has undergone changes over the course of time, the desire for a flawless outward appearance has always been the aim of human beings. The condition and the appearance of the skin is a significant part of a beautiful and attractive outward appearance. Regular cleansing and care are necessary to give the skin a flawless appearance.

Nowadays, consumers are offered a large number of cosmetic preparations for skin care, generally in the form of creams and lotions, i.e., as an emulsion. Products that temporarily or permanently delay or remove signs of aging in the skin (in particular the development of fine lines and wrinkles) thereby have steadily increasing importance. In addition to water for moisturizing the skin and oils and lipids for regreasing the skin, skin care products of this type contain a plurality of active substances, auxiliaries and additives.

The "aging skin" of older people differs from the "normal skin" of younger people in a plurality of symptoms. It is generally drier and shows an uneven hornification. Through its lack of water-binding capacity in the corium, deep wrinkles develop. The tendency of the epidermis to form vesicular flaking is increased. The appearance of old skin develops in genetic aging as with chronic environmental damage, as is caused, e.g., by excessive UV exposure.

Exogenous factors, such as UV light and chemical noxae, can have a cumulative effect and, e.g., accelerate or supplement the endogenous aging processes. In the epidermis and dermis, for example, the following structural damage and functional disorders appear in the skin as a result of exogenous factors:

a) Visible telangiectasis (cuperosis);
b) Flaccidity and the development of wrinkles;
c) Local hyperpigmentation, hypopigmentation and defective pigmentation (e.g., age spots);
d) Increased susceptibility to mechanical stress (e.g., cracking)
e) Decrease in the collagen content of the skin (e.g., through reduced new synthesis and/or through increased decomposition)
f) Disturbances in the glycosaminoglycan and elastin metabolism.

Over the past years skin research has developed or discovered a large number of active substances with which skin aging manifestations can be cosmetically treated and the visually perceptible skin aging process can be slowed down.

Conventional skin care products for the prophylaxis and treatment of skin aging symptoms, however, have the disadvantage that these active substances as a rule can be incorporated into cosmetic formulations only with difficulty and in unsatisfactory amounts. Furthermore, according to the prior art the disadvantage regularly occurs that combinations of active substances are difficult to incorporate into the preparations, since the active substances can exhibit incompatibility not only with the "carrier preparation" but also among one another.

The object of the present invention was to develop a new, stable and cosmetically effective skin care preparation for the prophylaxis and treatment of skin aging manifestations, in particular fine lines and wrinkles. In particular the skin's moisture should be increased by the skin care preparation.

The objects were surprisingly attained through a cosmetic preparation containing a combination of active substances of 0.001 to 3% by weight of hyaluronic acid and 0.01 to 4% by weight of saponins, the weight data being based on the total weight of the preparation.

Furthermore, the objects were surprisingly achieved through a cosmetic preparation containing a combination of 0.001 to 3% by weight of hyaluronic acid and 0.01 to 8% by weight of leguminose extract, which contains 0.01 to 99% by weight of saponins, the weight data of the hyaluronic acid and the leguminose extract being based on the total weight of the preparation and the weight data of the saponins being based on the total weight of the leguminose extract.

In particular, the objects are surprisingly attained through a cosmetic preparation containing a combination of 0.001 to 3% by weight of hyaluronic acid and 0.01 to 8% by weight of soy extract, which contains 0.01 to 99% by weight of saponins, the weight data for the hyaluronic acid and the soy extract being based on the total weight of the preparation and the weight data for the saponins being based on the total weight of the soy extract It has proven to be particularly advantageous according to the invention thereby, if the weight ratio of hyaluronic acid to saponins is from 1:1 to 1:10.

SUMMARY OF THE INVENTION

The present invention provides a cosmetic preparation. The preparation comprises, based on the total weight of the preparation:

(a) from 0.001% to 3% by weight of hyaluronic acid; and (b) (i) from 0.01% to 4% by weight of one or more saponins; or (ii) from 0.01% to 8% by weight of a leguminose extract or a soy extract which comprises, based on the total weight of the extract, from 0.01% to 99% by weight of one or more saponins.

In one aspect of the preparation, component (b) thereof may comprise one or more saponins from glycosides of triterpene sapogenins and may optionally further comprise one or more saponins from glycosides of steroid sapogenins. In another aspect, the preparation may be present as an O/W emulsion. In yet another aspect, the preparation may comprise a lipid phase with a total polarity of less than 30 mN/m. In a still further aspect of the preparation, the weight ratio of hyaluronic acid to the one or more saponins may be from 1:1 to 1:10.

The present invention also provides a cosmetic preparation which is present as an O/W emulsion and comprises, based on the total weight of the preparation:
(a) from 0.001% to 3% by weight of hyaluronic acid; and
(b) (i) from 0.01% to 4% by weight of one or more saponins; or
  (ii) from 0.01% to 8% by weight of a leguminose extract or a soy extract which comprises, based on the total weight of the extract, from 0.01% to 99% by weight of one or more saponins. The preparation further comprises a lipid phase with a total polarity of less than 30 mN/m.

In one aspect of the preparation, the weight ratio of hyaluronic acid to the one or more saponins may be from 1:1 to 1:10 and/or component (b) thereof may comprise one or more saponins from glycosides of triterpene sapogenins and, optionally, one or more saponins from glycosides of steroid sapogenins.

The present invention also provides a method for producing the cosmetic preparation of the present invention as an emulsion. The method comprises either (a) dissolving the one or more saponins or the extract comprising one or more saponins in an at least four-fold quantity of a glycol with a log P value between −3.6 and 1 to form a solution, and (b) adding the solution of (a) to a pre-emulsion; or (a) dispersing the one or more saponins or the extract comprising one or more saponins in an aqueous phase of the preparation, which aqueous phase comprises an at least four-fold quantity of the one or more saponins or the extract of a glycol with a log P value between −3.6 and 1 to form a dispersion, and (b) adding the dispersion of (a) to a fat phase of the emulsion, which fat phase may comprise one or more emulsifiers.

The present invention also provides a method for the prophylaxis and/or treatment of signs of skin aging. The method comprises applying to at least parts of the skin the preparation of the present invention as set forth above (including the various aspects thereof).

In one aspect of the method, the signs of skin aging may comprise fine lines and wrinkles.

The present invention also provides a method for making a cosmetic for treating signs of skin aging. The method comprises employing for the production of the cosmetic a combination of, based on the total weight of the cosmetic,
(a) from 0.001% to 3% by weight of hyaluronic acid; and
(b) (i) from 0.01% to 4% by weight of one or more saponins; or
  (ii) from 0.01% to 8% by weight of a leguminose extract or a soy extract which comprises, based on the total weight of the extract, from 0.01% to 99% by weight of one or more saponins.

DETAILED DESCRIPTION OF THE INVENTION

Advantageous embodiments of the invention are characterized in that the preparation contains saponins from glycosides of triterpene sapogenins in addition to optionally further saponins from glycosides of steroid sapogenins.

Hyaluronic acid is a glycosaminoglycan occurring in the vitreous body of the eye, the synovial fluid of the joints and in the skin, which together with chrondroitin sulfates and dermatan sulfate is a constituent of all connective tissue (apart from cornea).

Hyaluronic acid is a high molecular weight compound with $M_R$ between 50,000 and several million. The basic unit of hyaluronic acid is an aminodisaccharide constituted by D-gluconic acid and N-acetyl-D-glucosamine in β-(1→3)-glycosidic bonding, which is β-(1→4)-glycosidically linked to the next unit:

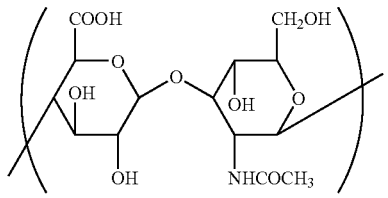

The sodium salt of the hyaluronic acid is used as moisturizer for the production of cosmetic agents (Römpp online Lexikon Version 2.5, 2004).

Saponin (from the Latin "sapo" for soap) is used to designate a group of generally vegetable glycosides that as surface-active compounds form colloidal saponaceous solutions.

Saponins are subdivided according to the type of their aglykones, the sapongenins, into triterpene saponins and steroid saponins. The carbohydrate content can consist of up to 11 monosaccharide radicals (mostly D-glucose, D-galactose, L-rhamnose, L-arabinose, D-xylose, D-fucose, D-glucuronic acid).

The most important saponins occurring in foodstuffs, the oleanoic acid saponins (beetroot), glycyrrhizine (licorice root) and the soybean saponins belong to the family of triterpene-saponins.

In cosmetics, saponins are used as humectants and dispersing agents or foaming agents with tooth powders, mouthwashes and shampoos (Römpp online Lexikon Version 2.5, 2004).

Although the active substances according to the invention are known to one skilled in the art in the field of cosmetics, it has not been possible hitherto to incorporate the combination of hyaluronic acid and saponins into cosmetic preparations, in particular emulsions, in a stable manner and effective form. For instance, according to the prior art the problem always arose with the combination of the two active substances that the homogeneous incorporation of the two raw materials was not possible according to a standard method. It was thus not possible either to guarantee a constant active substance concentration, particularly over a longer period. Both raw materials cannot be incorporated via the lipid phase, since they contain hydrophilic molecular constituents. But incorporation of the two raw materials via the aqueous phase is not possible either, since the saponins and hyaluronic acid cannot be homogeneously dissolved/dispersed in the aqueous phase simultaneously without forming cloudiness/crystals.

It was now possible to solve the problem according to the invention by developing a special method for producing a cosmetic preparation containing saponins as well as hyaluronic acid: the saponins or the plant extract containing the saponins is hereby first mixed with at least four times the quantity of a glycol with a log P value between −3.6 and 1 and dissolved with constant stirring and heating. Subsequently the solution is added to the pre-emulsion that is still warm if possible. Alternatively, the saponin can also be incorporated into the aqueous phase of the preparation, which contains at least four times the saponin quantity of corresponding glycol: while being heated and stirred constantly, the poorly soluble substance is stirred in and dispersed and subsequently combined with the fat phase, which contains the emulsifiers. It proved advantageous in both cases to stir and pre-swell the hyaluronic acid separately in a multiple quantity of water, so that a gel is formed. This is added to the emulsion, which is no longer very hot, while being stirred.

Within the scope of the present invention, the preparations according to the invention per se and the preparations produced according to the method according to the invention and the preparations used according to the invention are understood to be in accordance with the invention or preparations according to the invention.

It is advantageous according to the invention if the preparation according to the invention contains saponins based on triterpene sapogenines. In the use of soy saponin, these are in particular saponins from soy sapogenol A or soy sapogenol B. However, optionally saponins on the basis of steroid sapogenines can also be contained.

The leguminose extracts (fabaceae fam.) are preferably selected from representatives of the genera *abrus, anagyris, andira, anthyllis, arachis, aspalathus, astragalus, baptistia, canavalia, castanospermum, cicer, crotalaria, cyamopsis, cytisus, derris, dipteryx, galega, genista, glycine, glycyrrhiza, gymnoclamdus, indigofera, laburnum, lathyrus, lens, lespedeza, medicago, melilotus, mucuna, myroxylon, ononis, oxytropis, phaseolus, physostigma, piptadenia, psicidia, pisum, pterocarpus, robinia, sophora, trifolium, trigonella, ulex, vigna, vicia* and *wisteria.*

Extracts of soybean (*glycine soja*), field bean (*vicia faba*), garden bean (*phaseolus vulgaris*), linamarin (*phaseolus lunatus*), mung bean (*phaseolus aureus* and *vigna radiata*), lentil (*lens culinaris*), alfalfa (*medicago sativa*), Chinese tragacanth (*astragalus membranaceus*), peas (*pisum sativum*), blackgram (*vigna mungo*), adzuki bean (*vigna angularis*), licorice (*glycyrrhiza glabra*), peanut (*arachis hypogaea*), sophora (*sophora favescens*), goatsrue (*galega officinalis*), chickpeas (*cicer arietinum*), locoweed (oxytropis), sunn hemp (*crotalaria juncea*), Japanese wisteria (*wisteria floribunda*) and white clover (*trifolium repens*) are particularly suitable hereby.

If the saponins according to the invention are present in the form of a soy extract, it is advantageous according to the invention if the soy extract is standardized to the sapogenin content. As natural products, soy extracts contain a plurality of compounds, the most important representatives of which are the fats, carbohydrates, proteins, isoflavones, lecithins and saponins. Depending on the extraction method, the extracts can contain different ingredients. For example, there are soy oils or soy extracts that contain at least 90% isoflavonoids. Those soy extracts are advantageous according to the invention which have a high content of saponins. These should represent an enrichment of saponin compared to the content in the soybean. The soybean contains approx. 6.5 mg/g saponins. The extract should contain at least 10 mg/g, but particularly advantageously even over 100 mg/g saponin. One example of an extract that is suitable according to the invention is the soybean germ extract from Lucas Meyer Beauty Essentials with an approximate saponin content of 140 mg/g. This is a yellowish powder with a slight inherent smell of roasted nuts.

It is preferred according to the invention if the preparation according to the invention is present in the form of an emulsion and according to the invention particularly preferable if the preparation is present in the form of an O/W emulsion.

It is thereby advantageous for the purposes of the present invention if the preparation contains one or more of the following emulsifiers or emulsifier combinations: polyglyceryl-2 dipolyhydroxystearate, PEG-30 dipolyhydroxystearate, cetyldimethicone copolyol, glycol distearate, glycol dilaurate, diethylene glycol dilaurate, sorbitan trioleate, glycol oleate, glyceryl dilaurate, sorbitan tristearate, propylene glycol stearate, propylene glycol laurate, propylene glycol distearate, sucrose distearate, PEG-3 castor oil, pentaerythrityl monostearate, pentaerythrityl sesquioleate, glyceryl oleate, glyceryl stearate, glyceryl diisostearate, pentaerythrityl monooleate, sorbitan sesquioleate, isostearyl diglyceryl succinate, glyceryl caprate, palm glycerides, cholesterol, lanolin, glyceryl oleate (containing 40% monoester), polyglyceryl-2 sesquiisostearate, polyglyceryl-2 sesquioleate, PEG-20 sorbitan beeswax, sorbitan oleate, sorbitan isostearate, trioleyl phosphate, glyceryl stearate and ceteareth-20 (Teginacid from Th. Goldschmidt), sorbitan stearate, PEG-7 hydrogenated castor oil, PEG-5 soya sterol, PEG-6 sorbitan beeswax, glyceryl stearate SE, methylglucose sesquistearate, PEG-10 hydrogenated castor oil, sorbitan palmitate, PEG-22/dodecyl glycol copolymer, polyglyceryl-2 PEG-4 stearate, sorbitan laurate, PEG-4 laurate, polysorbate 61, polysorbate 81, polysorbate 65, polysorbate 80, triceteareth-4 phosphate, triceteareth-4 phosphate and sodium $C_{14-17}$-alkyl sec sulfonate (Hostacerin CG from Hoechst), glyceryl stearate and PEG-100 stearate (Arlacel 165 from ICI), polysorbate 85, trilaureth-4 phosphate, PEG-35 castor oil, sucrose stearate, trioleth-8 phosphate, $C_{12-15}$-Pareth-12, PEG-40 hydrogenated castor oil, PEG-16 soya sterol, polysorbate 80, polysorbate 20, polyglyceryl-3 methylglucose distearate, PEG-40 castor oil, sodium cetearyl sulphate, lecithin, laureth-4 phosphate, propylene glycol stearate SE, PEG-25 hydrogenated castor oil, PEG-54 hydrogenated castor oil, glyceryl stearate SE, PEG-6 caprylic/capric glycerides, glyceryl oleate and propylene glycol, glyceryl lanolate, polysorbate 60, glyceryl myristate, glyceryl isostearate and polyglyceryl-3 oleate, glyceryl laurate, PEG-40 sorbitan peroleate, laureth-4, glycerol monostearate, isostearyl glyceryl ether, cetearyl alcohol and sodium cetearyl sulphate, PEG-22 dodecylglycol copolymer, polyglyceryl-2 PEG-4 stearate, pentaerythrityl isostearate, polyglyceryl-3 diisostearate, sorbitan oleate and hydrogenated castor oil and cera alba and stearic acid, sodium dihydroxycetyl phosphate and isopropyl hydroxycetyl ether, methylglucose sesquistearate, methylglucose dioleate, sorbitan oleate and PEG-2 hydrogenated castor oil and ozokerite and hydrogenated castor oil, PEG-2 hydrogenated castor oil, PEG-45/dodecylglycol copolymer, methoxy PEG-22/dodecylglycol copolymer, hydrogenated cocoglycerides, polyglyceryl-4 isostearate, PEG-40 sorbitan peroleate, PEG-40 sorbitan perisostearate, PEG-8 beeswax, laurylmethicone copolyol, polyglyceryl-2 laurate, stearamidopropyl PG dimonium chloride phosphate, PEG-7 hydrogenated castor oil, triethyl citrate, glyceryl stearate citrate, cetyl phosphate polyglycerol methylglucose distearate, poloxamer 101, potassium cetyl phosphate, glyceryl isostearate, polyglyceryl-3 diisostearates.

Particularly advantageous according to the invention are O/W emulsifiers from the group of fatty acids, which are neutralized completely or partially with conventional alkalis (such as, e.g., sodium and/or potassium hydroxide, sodium and/or potassium carbonate and mono- and/or triethanolamine). Stearic acid and stearates, isostearic acid and isostearates, palmitic acid and palmitates and myristic acid and myristates, for example, are particularly advantageous.

The O/W emulsifier(s) are preferably selected from the following group: PEG-9-stearate, PEG-8-distearate, PEG-20-stearate, PEG-8-stearate, PEG-8-oleate, PEG-25-glyceryltrioleate, PEG-40-sorbitan lanolate, PEG-15-glyceryl ricinoleate, PEG-20-glyceryl stearate, PEG-20-glyceryl isostearate, PEG-20-glyceryl oleate, PEG-20-stearate, PEG-20-methylglucose sesquistearate, PEG-30-glyceryl isostearate, PEG-20-glyceryl laurate, PEG-30-stearate, PEG-30-glyceryl stearate, PEG-40-stearate, PEG-30-glyceryl laurate, PEG-50-stearate, PEG-100-stearate, PEG-150-laurate. For example, polyethoxylated esters of stearic acid are particularly advantageous.

The coemulsifier(s) are advantageously selected according to the invention from the following group: butyloctanol, butyldecanol, hexyloctanol, hexyldecanol, octyldodecanol, behenyl alcohol ($C_{22}H_{45}OH$), cetearyl alcohol [a mixture of cetyl alcohol ($C_{16}H_{33}OH$) and stearyl alcohol ($C_{18}H_{37}OH$)], lanolin alcohols (wool alcohols that represent the unsaponifiable alcohol fraction of wool grease which is obtained after the saponification of wool grease). Cetyl alcohol and cetylstearyl alcohol are particularly preferred.

Embodiments of the invention that are preferred according to the invention are characterized in that the preparation has a lipid phase with a total polarity of less than 30 mN/m.

The total polarity of the lipid phase is thereby determined according to the invention as follows:

| | |
|---|---|
| Measuring instrument: | Ring tensiometer (e.g., Krüss K 10) |
| Measured quantity: | Specific interfacial energy = interfacial tension [unit: mN/m] |
| Lower limit: | 5 mN/m |

The lipid phase can advantageously be chosen from the following group of substances:

Mineral oils, mineral waxes

Oils, such as triglycerides of capric acid or of caprylic acid, and also natural oils, such as, for example, castor oil, macadamia oil, avocado oil or jojoba oil, dialkyl ethers, such as, for example, di-n-octyl ethers, and dialkyl carbonates, such as, for example, di-n-octyl carbonate Fats, waxes and other natural and synthetic fatty bodies, preferably esters of fatty acids with alcohols of low carbon number, e.g. with isopropanol, propylene glycol or glycerol, or esters of fatty alcohols with alkanoic acids of low carbon number or with fatty acids;

Alkyl benzoates;

Silicone oils, such as dimethylpolysiloxanes, diethylpolysiloxanes, diphenylpolysiloxanes, and mixed forms thereof.

The oil phase of the emulsions, hydrodispersions or lipodispersions for the purposes of the present invention is advantageously selected from the group of the esters of saturated and/or unsaturated, branched and/or unbranched alkanecarboxylic acids with a chain length from 3 to 30 C atoms, and saturated and/or unsaturated, branched or unbranched alcohols with a chain length from 3 to 30 C atoms, from the group of the esters of aromatic carboxylic acids and saturated and/or unsaturated, branched and/or unbranched alcohols with a chain length from 3 to 30 C atoms. Such ester oils can then be advantageously selected from the group of isopropyl myristate, isopropyl palmitate, isopropyl stearate, isopropyl oleate, n-butyl stearate, n-hexyl laureate, n-decyl oleate, isooctyl stearate, isononyl stearate, isononyl isononanoate, 2-ethylhexyl palmitate, 2-ethylhexyl laureate, 2-hexyldecyl stearate, 2-octyldocecyl palmiate, oleyl oleate, oleyl erucate, erucyl oleate, erucyl erucate, as well as synthetic, semisynthetic, and natural mixtures of such esters, for example, jojoba oil.

Furthermore, one may advantageously select the oil phase from the group of branched and unbranched hydrocarbons and hydrocarbon waxes, silicone oils, dialkylethers, the group of saturated or unsaturated, branched or unbranched alcohols, as well as the fatty acid triglycerides, namely the triglycerin ester of saturated and/or unsaturated, branched and/or unbranched alkanoic acids of a chain length of 8 to 24, in particular 12 to 18 C atoms. One may advantageously select the fatty acid triglycerides, for example, from the group of the synthetic, semisynthetic, and natural oils, for example, olive oil, sunflower oil, soy bean oil, peanut oil, rape seed oil, almond oil, palm oil, coconut oil, palm kernel oil, and more of the like.

Likewise, blends of such oil and wax components may advantageously be used for the purposes of the present invention. Optionally, it can also be advantageous to use waxes, for example, cetyl palmitate as the sole lipid component of the oil phase.

The oil phase is advantageously chosen from the group of 2-ethylhexyl isostearate, octyldodecanol, isotridecyl isononanoate, isoeicosane, 2-ethylhexylcocoate, $C_{12-15}$-alkylbenzoate, caprylic/capric acid triglyceride, and dicaprylyl ether.

Especially advantageous are mixtures of $C_{12-15}$-alkylbenzoate and 2-ethylhexyl isostearate, mixtures of $C_{12-15}$-alkylbenozate and isotridecyl isononanoate, as well as mixtures of $C_{12-15}$-alkylbenzoate, 2-ethylhexyl isostearate and isotridecyl isononanoate.

Of the hydrocarbons, paraffin oil, squalane and squalene may be used advantageously for the purposes of the present invention.

Advantageously, the oil phase may further include a content of cyclic or linear silicone oils or may be composed entirely of such oils. However, besides the silicone oil or oils, it is preferred to use an additional content of other oil phase components.

Cyclomethicone (octamethyl cyclotetrasiloxane) is advantageously used as silicone oil to be used in accordance with the invention. However, other silicone oils can also be used advantageously for the purposes of the present invention, for example, hexamethyl cyclotrisiloxane, polydimethylsiloxane, and poly(methylphenylsiloxane).

Other particularly advantageous mixtures are those of cyclomethicone and isotridecyl isononanoate, of cyclomethicone and 2-ethylhexyl isostearate.

Optionally, the aqueous phase of the preparations according to the invention advantageously comprises alcohols, diols, or polyols having a low number of C atoms, as well ethers thereof, preferably ethanol, isopropanol, propylene glycol, glycerin, ethyleneglycol, ethyleneglycol monoethyl- or -monobutyl ether, propylene glycolmonomethyl, -monoethyl-, or -monobutyl ether, diethyleneglycol monomethyl- or -monoethyl ether, and analogous products, furthermore alcohols having a low number of C atoms, for example, ethanol, isopropanol, 1,2-propanediol, 2-methyl-1,3-propanediol, glycerin, as well as in particular one or more thickeners.

The cosmetic preparations according to the invention can comprise cosmetic auxiliaries as are customarily used in such preparations, e.g., preservatives, bactericides, perfumes, substances for preventing foaming, dyes, pigments which have a coloring effect, thickeners, surface-active substances, emulsifiers, softening, moisturizing and/or humectant substances, fats, oils, waxes or other customary constituents of a cosmetic or dermatological formulation, such as complexing agents, alcohols, polyols, polymers, foam stabilizers, electrolytes, organic solvents or silicone derivatives, plant extracts, vitamins, perfumes.

In particular, active substance combinations used according to the invention can also be combined with the antioxidants and/or radical scavengers known in cosmetics.

Preparations according to the invention can advantageously also contain substances which absorb UV radiation in the UVB range, the total amount of the filter substances being, for example, from 0.1% by weight to 30% by weight, preferably 0.5% to 10% by weight, in particular 1.0% to 6.0% by weight, based on the total weight of the preparations, in order to provide cosmetic preparations which protect the hair or the skin from the entire range of ultraviolet radiation. They can also be used as sunscreen for the hair.

If the preparations according to the invention contain UVB filter substances, these can be oil-soluble or water-soluble. Advantageous oil-soluble UVB filters according to the present invention include, e.g.:

3-benzylidenecamphor derivatives, preferably 3-(4-methylbenzylidene)camphor, 3-benzylidenecamphor;

4-aminobenzoic acid derivatives, preferably (2-ethylhexyl) 4-(dimethylamino)-benzoate, amyl 4-(dimethylamino)benzoate;

Esters of cinnamic acid, preferably 2-ethylhexyl 4-methoxycinnamate, isopentyl 4-methoxycinnamate;

Esters of salicylic acid, preferably 2-ethylhexyl salicylate, 4-isopropylbenzyl salicylate, homomenthyl salicylate;

Derivatives of benzophenone, preferably 2-hydroxy-4-methoxybenzophenone, 2-hydroxy-4-methoxy-4'-methylbenzophenone, 2,2'-dihydroxy-4-methoxy-benzophenone;

Esters of benzalmalonic acid, preferably 2-ethylhexyl 4-methoxybenzalmalonate;

Esters of 2-cyano-3,3-diphenylacrylic acid, preferably ethylhexyl-2-cyano-3,3-diphenyl acrylate, Diethylhexyl-butamidotriazone, 2,4,6-trianilino-(p-carbo-2'-ethyl-1'-hexyloxy)-1,3,5-triazine.

Advantageous water-soluble UVB filters are, for example:

Salts of 2-phenylbenzimidazole-5-sulfonic acid, such as its sodium, potassium, or its triethanolammonium salt, and the sulfonic acid itself;

Sulfonic acid derivatives of benzophenones, preferably, 2-hydroxy-4-methoxybenzophenone-5-sulfonic acid and its salts;

Sulfonic acid derivatives of 3-benzylidene camphor, such as, for example, 4-(2-oxo-3-bornylidenemethyl)benzenesulfonic acid, 2-methyl-5-(2-oxo-3-bornylidenemethyl)sulfonic acid and its salts and 1,4-di(2-oxo-10-sulfo-3-bornylidenemethyl)benzene and salts thereof (the corresponding 10-sulfato compounds, e.g., the corresponding sodium, potassium or triethanolammonium salts) also called benzene- 1,4-di(2-oxo-3-bornylidenmethyl-10-sulfonic acid.

The list of the cited UVB filters that can be used in combination with the active substance combinations according to the invention is naturally not intended to be limiting.

It can also be advantageous to use UVA filers that are customarily contained in cosmetic preparations. These substances are preferably derivatives of dibenzoylmethane, in particular 1-(4'-tert.butylphenyl)-3-(4'-methoxyphenyl)-propane-1,3-dione and 1-phenyl-3-(4' -isopropylphenyl)propane-1,3-dione.

Furthermore advantageous UVA filters come from the group of triazines, such as, e.g., 2,4-bis{[4-(2-ethylhexyloxy)-2-hydroxy]phenyl}-6-(4-methoxyphenyl)-1,3,5-triazine (trade name: Tinosorb® S), and the group of triazoles, such as, e.g., 2,2'-methylene-bis[6-(2H-benzotriazol-2-yl]-4-(1,1,3,3-tetramethylbutyl)phenol) (trade name Tinosorb® M). An advantageous water-soluble UVA filter is 2'-bis(1,4-phenylene)-1H-benzimidazole-4,6-disulfonic acid sodium salt (trade name Neo Heliopan AP®).

The quantities used for the UVB combination can be used.

Preferred inorganic pigments are metal oxides and/or other metal compounds that are poorly soluble or insoluble in water, in particular oxides of titanium ($TiO_2$), zinc (ZnO), iron (e.g., $Fe_2O_3$), zirconium ($ZrO_2$), silicon ($SiO_2$), manganese (e.g., MnO), aluminum ($Al_2O_3$), cerium (e.g., $Ce_2O_3$), mixed oxides of the corresponding metals and mixtures of such oxides and the sulfate of barium ($BaSO_4$).

Advantageously for the purposes of the present invention the pigments can also be used in the form of commercially available oleaginous or aqueous predispersions. Dispersing agents and/or solubilizers can advantageously be added to these predispersions.

The pigments can advantageously be surface-treated ("coated"), in which case, for example, the intention is to form and/or retain a hydrophilic, amphiphilic or hydrophobic character. This surface treatment can comprise providing the pigments with a thin hydrophilic and/or hydrophobic inorganic and/or organic layer by methods known per se. For the purposes of the present invention, the various surface coatings can also contain water.

Inorganic surface coatings within the scope of the present invention can comprise aluminum oxide ($Al_2O_3$), aluminum hydroxide $Al(OH)_3$ or aluminum oxide hydrate (also: alumina, CAS No.: 1333-84-2), sodium hexametaphosphate ($NaPO_3)_6$, sodium metaphosphate ($NaPO_3)_n$, silicon oxide ($SiO_2$) (also: silica, CAS No.: 7631-86-9), or iron oxide ($Fe_2O_3$). These inorganic surface coatings can occur alone or in combination and/or in combination with organic coating materials.

Organic surface coatings within the scope of the present invention can consist of vegetable or animal aluminum stearate, vegetable or animal stearic acid, lauric acid, dimethylpolysiloxane (also: dimethicone), methylpolysiloxane (methicone), simethicone (a mixture of dimethylpolysiloxane with an average chain length of 200 to 350 dimethylsiloxane units and silica gel) or alginic acid. These organic surface coatings can occur alone, in combination and/or in combination with inorganic coating materials.

The method for producing the cosmetic preparation according to the invention is according to the invention as well, which method is characterized in that the saponins or the soy extract containing the saponins is first dissolved in at least four times the quantity of a glycol with a log P value between −3.6 and 1 or in the aqueous phase of the preparation that contains this quantity of the glycol, and is subsequently combined with a fat phase containing the emulsifiers.

The log P value according to the invention is thereby calculated according to the following program:

| | |
|---|---|
| Manufacturer: | Advanced Chemistry Development Inc. (ACD) 90 Adelaide Street West, Suite 702 Toronto, Canada |
| Program: | ACD/LogD Suite v. 4.5 |

The use of the cosmetic preparation according to the invention or the active substance combination of hyaluronic acid and saponins according to the invention for the cosmetic prophylaxis and/or treatment of skin aging manifestations, in particular fine lines and wrinkles, is according to the invention.

The use of an active substance combination according to the invention (i.e., the active substance combination of 0.001 to 3% by weight of hyaluronic acid and 0.01 to 4% by weight of saponins, or 0.001 to 3% by weight of hyaluronic acid and 0.01 to 8% by weight of leguminose extract containing 0.01 to 99% by weight of saponins) for the production of a cosmetic for treating skin aging manifestations, in particular fine lines and wrinkles, is according to the invention. The plant extract is preferably soybean extract.

These uses are according to the invention when the cosmetic or the cosmetic preparation is applied topically to the skin.

According to the invention the prophylaxis and treatment within the scope of this disclosure mean exclusively cosmetic prophylaxis and treatment, and on no account a therapeutic prophylaxis and treatment as defined by patent law.

The uses according to the invention are used in particular in skin creams or face creams, skin lotions or face lotions and day or night creams or lotions.

The following examples are designed to clarify the present invention without restricting it. All quantities, proportions and percentages are based on the weight and the total quantity or on the total weight of the preparations, unless stated otherwise.

EXAMPLES

Examples 1-10

O/W Creams

| Example Number | 1 | 2 | 3 | 4 | 5 |
|---|---|---|---|---|---|
| Glyceryl stearate citrate | 2 | | | 2 | |
| Glyceryl stearate, self-emulsifying | | 5 | 3 | | 2 |
| PEG-40-Stearate | | | 1 | | 1 |
| Myristyl myristate | 1 | | | | 1 |
| Behenyl alcohol | | | | | |
| Stearyl alcohol | 2 | 1 | | | |
| Cetearyl alcohol | | | | 4 | 2 |
| Cetyl alcohol | 1 | | 3 | | |
| Hydrogenated coco-glycerides | 2 | | | | |
| Shea butter | | 2 | | | 2 |
| C12-15 Alkylbenzoate | | 3 | 2 | | 3 |
| Butylene glycol dicaprylate/dicaprate | 1 | | | 1 | |
| Caprylic acid/capric acid triglyceride | | 1 | 1 | 2 | 2 |
| Ethylhexyl coconut fatty acid ester | 3 | | | | 1 |
| Octyldodecanol | | | 1 | | |
| Mineral oil | | 1 | | | |
| Petrolatum | 2 | | 1 | | 2 |
| Octamethyltetrasiloxane (cyclomethicon) | 4 | 1 | | 3 | 5 |
| Dimethylpolysiloxane (Dimethicon) | | | | 1 | |
| Dicaprylyl ether | 1 | | 2 | | |
| Dicaprylyl carbonate | | | | 3 | |
| TiO$_2$ | | | | 2 | |
| Ethylhexyl methoxycinnamate | | | | | 2 |
| Ethylhexyl cyanodiphenyl-acrylate (octocrylene) | | 3 | | | |
| Bis-ethylhexyloxyphenol methoxyphenyltriazine | | 0.5 | | | |
| Ethylhexyl salicylate | | | | | 1 |
| Glycine soja | 2 | | 1 | | 4 |
| *Vicia faba* | | 1 | | | |
| *Medicago sativa* | | | 1 | | |
| *Pisum sativum* | | | | 2 | |
| Hyaluronic acid | 0.01 | 0.1 | 0.05 | 1 | 0.6 |
| Ubiquinone (Q10) | 0.05 | | | | |
| Biotin | | | | | 0.04 |
| Retinol | | | | 0.1 | |
| Tocopheryl acetate | | | 1 | | |
| Citric acid, sodium salt | | 0.1 | | | |
| Sodium ascorbylphosphate | 0.1 | | | | |
| Trisodium EDTA | | 0.1 | | 0.2 | |
| Iminodisuccinate, sodium salt | 0.2 | | 0.1 | | 0.1 |
| Phenoxyethanol | 0.3 | | 0.3 | 0.2 | 0.2 |
| p-Hydroxybenzoic acid alkylester (paraben) | 0.6 | | 0.2 | 0.3 | 0.3 |
| Hexamidine diisethionate | | 0.04 | | | |
| Diazolidinyl urea | 0.25 | | 0.1 | | |
| 1,3-Dimethylol-5,5-dimethylhydantoin (DMDM Hydantoin) | | 0.2 | | | |
| Iodopropynyl butylcarbamate | | | 0.1 | | |
| Ethanol denatured | | 2 | | | |
| Xanthan gum | 0.1 | | | | |
| Polyacrylic acid (carbomer) | 0.05 | | 0.1 | | 0.1 |
| Polyacrylamide | | 0.2 | | | |
| 1,2,3-Propanetriol | 10 | 6 | | 7.5 | 18 |
| 1,3-Butanediol | 2 | 3 | 3 | | 2 |
| 2-Methyl-1,3-propanediol | | | | 1 | |

-continued

|  |  |  |  |  |  |
|---|---|---|---|---|---|
| 1,2-Propanediol |  |  | 5 |  |  |
| 1,5-Pentanediol |  |  | 2 |  |  |
| 1,2-Hexanediol |  |  |  | 1 |  |
| Water-soluble and/or oil-soluble dyes | 0.05 |  |  |  |  |
| Fillers/additives (distarch phosphate, SiO$_2$, BHT, talc, aluminium stearate) | 0.1 | 1 | 0.2 | 0.5 | 0.05 |
| Perfume | q.s. | q.s. | q.s. | q.s. | q.s. |
| Water | Ad 100 | Ad 100 | Ad 100 | Ad 100 | Ad 100 |

| Example Number | 6 | 7 | 8 | 9 | 10 |
|---|---|---|---|---|---|
| Glyceryl stearate, self-emulsifying | 2.5 |  |  |  |  |
| PEG-40-stearate | 1 |  |  |  |  |
| Polyglyceryl-3-methyl glucose distearate |  | 3 |  |  |  |
| Sorbitan stearate |  | 1 |  |  |  |
| Polyethylene glycol(21)stearyl-ether (steareth-21) |  |  | 2 |  |  |
| Polyethylene glycol(2)stearyl ether (steareth-2) |  |  | 1 |  |  |
| Cetearyl glucoside |  |  |  | 2 |  |
| Stearic acid |  |  |  |  | 2 |
| Myristyl myristate |  |  |  | 1 |  |
| Behenyl alcohol |  | 1 |  |  |  |
| Stearyl alcohol |  |  |  | 2 |  |
| Cetearyl alcohol | 3 |  | 2 |  | 2 |
| Cetyl alcohol |  | 1 |  |  |  |
| Hydrogenated coco-glycerides | 1 |  |  |  | 1 |
| Shea butter |  | 2 |  |  |  |
| C12-15 Alkyl benzoate | 4 |  | 5 | 2 |  |
| Butylenglycol dicaprylate/dicaprate |  |  |  |  | 2 |
| Caprylic acid/capric acid triglyceride | 1 | 1 |  | 3 |  |
| Hydrogenated polydecene |  |  |  | 1 |  |
| Ethylhexyl coconut fatty acid ester |  |  |  |  | 2 |
| Octyl dodecanol |  |  | 1 |  | 1 |
| Mineral oil |  |  | 1 |  |  |
| Octamethyl tetrasiloxane (Cyclomethicone) | 4 | 3 | 2 |  |  |
| Dimethyl polysiloxane (Dimethicone) |  |  |  |  | 1 |
| Dicaprylyl ether |  |  | 2 |  |  |
| Dicaprylyl carbonate |  | 2 |  | 3 | 4 |
| Polydecene |  |  |  | 4 |  |
| Ethylhexyl methoxy-cinnamate |  | 3 |  |  |  |
| Phenylbenzimidazole sulfonic acid | 2 |  |  |  | 1 |
| Bis-ethylhexyloxyphenol methoxyphenyl triazine | 1 |  |  |  |  |
| Glycine soya | 0.5 | 2 |  |  |  |
| *Crotalaria juncea* |  |  | 1 |  |  |
| *Lens culinaris* |  |  |  | 4 |  |
| *Arachis hypogaea* |  |  |  |  | 1.5 |
| Hyaluronic acid | 0.05 | 0.2 | 0.3 | 1 | 0.01 |
| Ubiquinone (Q10) | 0.03 |  |  |  |  |
| Tocopherol |  | 1 |  |  | 0.5 |
| Lactoferrin |  |  |  |  | 0.05 |
| Trisodium EDTA |  |  | 0.2 | 0.1 |  |
| Iminodisuccinate | 0.2 | 0.2 |  |  | 0.1 |
| Phenoxyethanol | 0.5 | 0.4 | 0.5 |  | 0.3 |
| p-Hydroxybenzoic acid alkylester (paraben) | 0.1 |  |  | 0.4 | 0.6 |
| Hexamidine diisethionate |  |  | 0.1 |  |  |
| Diazolidinyl urea | 0.2 | 0.2 |  | 0.1 |  |
| Iodopropynyl butylcarbamate |  |  | 0.25 |  |  |
| Ethanol denatured |  | 8 |  |  | 3 |
| 2-ethylhexyl glycerol ether (octoxyglycerin) |  |  |  | 0.4 |  |
| Xanthan gum |  | 0.1 |  |  |  |
| Polyacrylic acid (carbomer) | 0.2 |  | 0.1 |  | 0.1 |
| Polyacrylamide |  | 0.2 |  |  |  |
| 1,2,3-Propanetriol | 10 | 6 |  | 20 | 6 |

-continued

| | | | | | |
|---|---|---|---|---|---|
| 1,3-Butanediol | | 3 | 3 | | 2 |
| 2-Methyl-1,3-propanediol | | | | | |
| 1,2-Propanediol | | 1 | 6 | | |
| 1,5-Pentanediol | | | | | 2 |
| 1,2-Hexanediol | | | 1 | | |
| Water-soluble and/or oil-soluble dyes | | | | | 0.1 |
| Additives (distarch phosphate, SiO$_2$, talcum, BHT aluminium stearate) | 0.03 | 0.1 | 0.05 | 3 | 1 |
| Perfume | q.s. | q.s. | q.s. | q.s. | q.s. |
| Water | Ad 100 | Ad 100 | Ad 100 | Ad 100 | Ad 100 |

What is claimed is:

1. A cosmetic preparation, wherein the preparation comprises, based on a total weight of the preparation:
   (a) from 0.001% to 3% by weight of hyaluronic acid; and
   (b) (i) from 0.01% to 4% by weight of one or more saponins; or
       (ii) from 0.01% to 8% by weight of a leguminose extract or a soy extract which comprises, based on a total weight of the extract, from 0.01% to 99% by weight of one or more saponins;
   and wherein the preparation comprises a lipid phase with a total polarity of less than 30 mN/m.

2. The preparation of claim 1, wherein the one or more saponins comprise glycosides of triterpene sapogenins.

3. The preparation of claim 2, wherein the one or more saponins further comprise glycosides of steroid sapogenins.

4. The preparation of claim 1, wherein the preparation is present as an O/W emulsion.

5. The preparation of claim 1, wherein a weight ratio of hyaluronic acid to the one or more saponins is from 1:1 to 1:10.

6. The preparation of claim 1, wherein the preparation comprises (b)(i).

7. The preparation of claim 1, wherein the preparation comprises (b)(ii).

8. The preparation of claim 7, wherein the preparation comprises a leguminose extract.

9. The preparation of claim 7, wherein the preparation comprises a soy extract.

10. The preparation of claim 4, wherein a weight ratio of hyaluronic acid to the one or more saponins is from 1:1 to 1:10.

11. The preparation of claim 4, wherein the preparation comprises (b)(i).

12. The preparation of claim 4, wherein the preparation comprises (b)(ii).

13. The preparation of claim 12, wherein the preparation comprises a leguminose extract.

14. The preparation of claim 12, wherein the preparation comprises a soy extract.

15. The preparation of claim 4, wherein the one or more saponins comprise glycosides of triterpene sapogenins.

16. The preparation of claim 15, wherein the one or more saponins further comprise glycosides of steroid sapogenins.

17. The preparation of claim 10, wherein the preparation comprises (b)(i).

18. The preparation of claim 10, wherein the preparation comprises (b)(ii).

19. The preparation of claim 18, wherein the preparation comprises a leguminose extract.

20. The preparation of claim 18, wherein the preparation comprises a soy extract.

* * * * *